United States Patent

Neal et al.

[11] Patent Number: 5,766,261
[45] Date of Patent: Jun. 16, 1998

[54] FEMORAL REVISION BROACH WITH MODULAR TRIAL COMPONENTS AND METHOD

[75] Inventors: David J. Neal, Mahwah; Gregory A. Guederian, Hackensack, both of N.J.

[73] Assignee: Osteonics Corp., Allendale, N.J.

[21] Appl. No.: 595,129

[22] Filed: Feb. 1, 1996

[51] Int. Cl.⁶ .................................. A61F 2/28; A61F 5/04
[52] U.S. Cl. .................................. 623/16; 606/85
[58] Field of Search .................. 606/79, 80, 85, 606/84; 623/16, 23

[56] References Cited

U.S. PATENT DOCUMENTS

| | | | |
|---|---|---|---|
| 5,100,407 | 3/1992 | Conrad et al. | |
| 5,169,401 | 12/1992 | Lester et al. | 606/79 |
| 5,169,402 | 12/1992 | Elloy | 606/85 |
| 5,211,645 | 5/1993 | Baumgart et al. | 606/79 |
| 5,261,915 | 11/1993 | Durlacher et al. | 606/79 |
| 5,403,320 | 4/1995 | Luman et al. | 606/79 |
| 5,441,501 | 8/1995 | Kenyon | 606/85 |
| 5,496,324 | 3/1996 | Barnes | 606/79 |

Primary Examiner—David Isabella
Attorney, Agent, or Firm—Arthur Jacob

[57] ABSTRACT

An improvement in a surgical instrument set and procedure for the preparation of a proximal femur to receive a revision femoral implant component includes a revision broach for mimicking a selected one of a plurality of revision femoral implant components and the insertion of the revision broach into the proximal femur to a location which emulates the location of the selected one of the plurality of revision femoral implant components, and utilizing a stop member positioned at a selected one of a plurality positions located longitudinally along the revision broach and corresponding to one of a plurality of resection levels determined by the selected revision femoral implant component to maintain the revision broach seated at the emulating location during subsequent trial reduction utilizing a trial neck and a trial head coupled to the revision broach.

12 Claims, 4 Drawing Sheets

FEMORAL REVISION BROACH WITH MODULAR TRIAL COMPONENTS AND METHOD

The present invention relates generally to revision surgery in connection with restoring the function of a hip joint and pertains, more specifically, to improvements in a surgical instrument set and procedure for accommodating different conditions encountered in the proximal femur at the site of the revision surgery.

Revision surgery often becomes necessary at the site of a hip implant in order to restore and maintain long-term mechanical stability, prevent additional bone loss, and restore leg-length, muscle balance and an adequate range of motion. Failure of a primary hip implant often leads to uncertainty in the condition of the natural bone at the implant site and the availability of natural bone for the reception of revision implant components. In particular, a variety of deficiencies in the proximal femur must be identified and addressed in pursuing the goals of revision surgery, as outlined above. As a result, a range of revision femoral implant components has been made available to accommodate the various deficiencies encountered at the proximal femur.

The present invention provides a set of modular surgical instruments in which a femoral revision broach is utilized to prepare the proximal femur for the reception of a revision femoral implant component, with a single revision broach serving to accommodate the various deficiencies encountered at the site of the revision surgery, to prepare the site for the reception of a revision femoral implant component selected from a plurality of revision femoral components constructed to compensate for different deficiencies encountered at the implant site. As such, the present invention attains several objects and advantages, some of which are summarized as follows: Provides a surgical instrument set incorporating a single revision broach which enables mimicking any one of a plurality of revision femoral implant components constructed to compensate for different deficiencies encountered in a proximal femur, for the conduct of trial reduction with the revision broach in place in the proximal femur; simplifies the revision procedure, enabling reduced operating time, with concomitant benefits to the patient; attains increased accuracy and precision in the location of an appropriate revision femoral implant component, without the necessity for multiple revision broaches to accommodate different conditions encountered at the implant site; provides a visual indication of the appropriate location of the single revision broach in the proximal femur, and maintaining seating of the revision broach at that location for the subsequent conduct of trial reduction; reduces the expense and complexity of a set of surgical instruments utilized for revision surgery; facilitates the revision surgery procedure.

The above objects and advantages, as well as further objects and advantages, are attained by the present invention which may be described briefly as an improvement in a surgical instrument set for the preparation of a proximal femur during surgery to receive a selected one femoral implant component of a plurality of available femoral implant components provided to accommodate a corresponding one of a plurality of resection levels determined by the condition of the proximal femur, the improvement including: a broach having a distal end for the reception of a selected distal extension to mimic the selected one femoral implant component, and a proximal end spaced longitudinally from the distal end for alternately receiving an operating handle for insertion of the broach into the proximal femur, and a trial neck and a trial head for conducting a trial reduction; a stop member; and selective attachment means for selectively attaching the stop member to the broach at any one selected location of a plurality of locations spaced longitudinally along the broach, the plurality of locations corresponding to the plurality of resection levels such that the stop member is juxtaposed with the proximal femur when the broach is at a location which emulates the location of the selected femoral implant component and maintains the broach seated at that location for reception of the trial neck and the trial head and subsequent trial reduction.

Additionally, the present invention includes an improvement in a method for the preparation of a proximal femur during surgery to receive a selected one femoral implant component of a plurality of available femoral implant components provided to accommodate a corresponding one of a plurality of resection levels determined by the condition of the proximal femur, the improvement including the steps of: coupling a selected distal extension and an operating handle to a broach having a distal end for the reception of the selected distal extension to mimic the selected one femoral implant component, a proximal end spaced longitudinally from the distal end for alternately receiving the operating handle and a trial neck and a trial head, and selective attachment means providing a plurality of attachment locations spaced longitudinally along the broach, the plurality of locations corresponding to the plurality of resection levels; inserting the broach into the proximal femur and placing the broach at a location where the corresponding one of the plurality of attachment locations is placed at the selected one of the plurality of resection levels so as to emulate the location of the selected femoral implant component in the proximal femur; attaching a stop member to the broach at the one of the plurality of attachment locations corresponding to the one of the plurality of resection levels for maintaining the broach seated at the location which emulates the location of the selected femoral implant component; detaching the operating handle from the proximal end of the broach; and attaching the trial neck and the trial head to the proximal end of the broach for subsequent trial reduction.

The invention will be understood more fully, while still further objects and advantages will become apparent, in the following detailed description of preferred embodiments of the invention illustrated in the accompanying drawing, in which.

Figure 1:
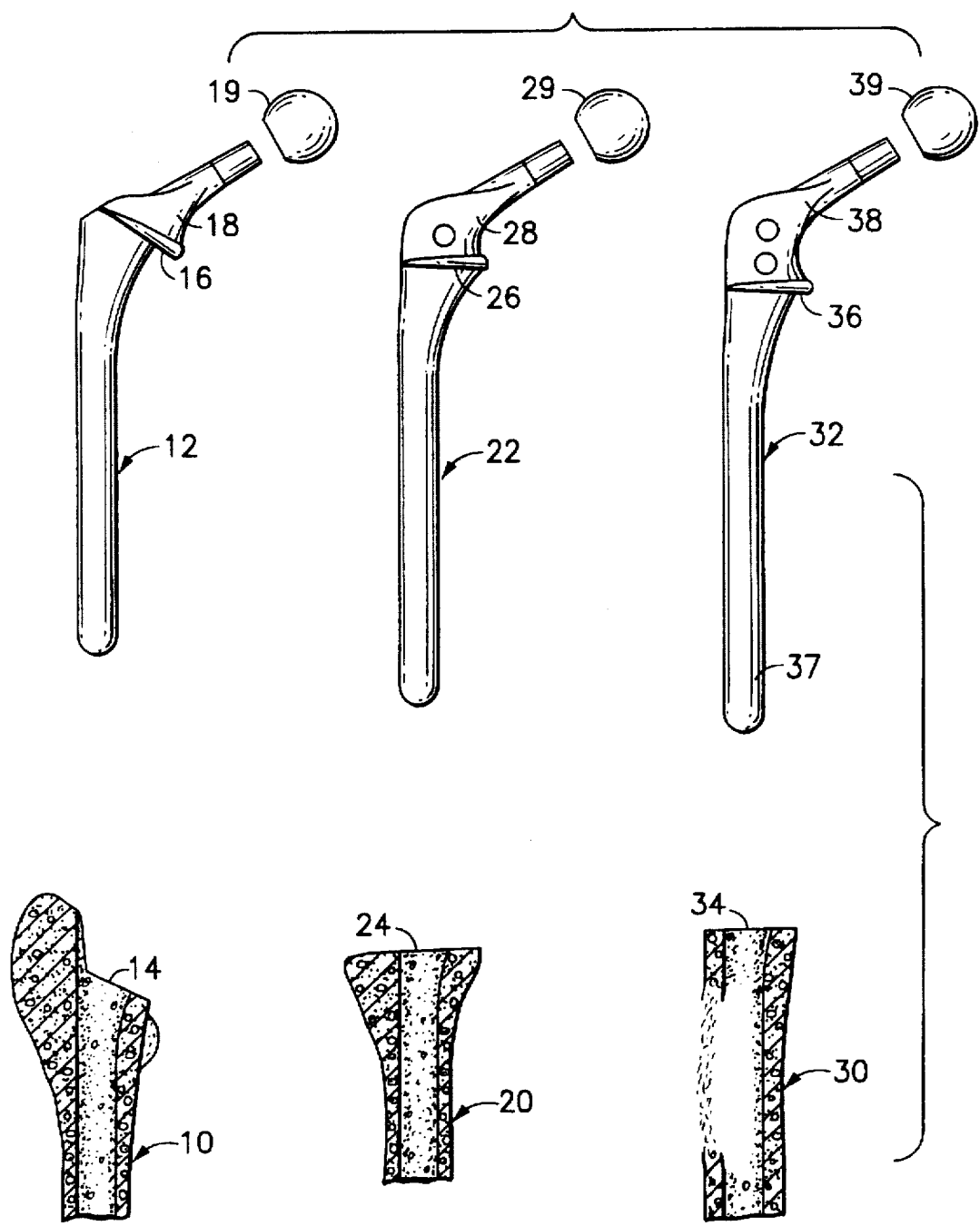
FIG. 1 is a series of fragmentary longitudinal cross-sectional views of typical proximal femurs illustrating various possible conditions encountered at a proximal femur during revision surgery, resection levels established for those different conditions, and diagrammatic views of corresponding revision femoral implant components constructed to accommodate the different conditions.

Referring now to the drawing, and especially to FIG. 1 thereof, a first proximal femur 10 is seen partially prepared for the reception of a revision femoral implant component, shown diagrammatically at 12, the preparation having included reaming and resection to establish a resection level at 14. Proximal femur 10 exhibits a defect in which some expansion of the metaphysis is present; however, the calcar and metaphysis are intact and the isthmus is undamaged. The revision femoral implant component 12 includes an integral collar 16 which will be seated upon the natural bone of the proximal femur 10 at the resection level 14. A neck portion 18 of the revision femoral implant component 12 then will receive a femoral head 19, in a conventional manner.

A second proximal femur 20 is seen partially prepared for the reception of a revision femoral implant component shown diagrammatically at 22. Here, the metaphysis has been compromised and resection has established a resection level at 24. The revision femoral component 22 includes an integral collar 26 which will be seated upon the natural bone of the proximal femur 20 at the resection level 24, and an extended neck portion 28 compensates for the absence of a portion of the calcar. A femoral head 29 will be coupled with the neck portion 28 in a known manner.

A third proximal femur 30 is seen partially prepared for the reception of a revision femoral implant component shown diagrammatically at 32. Extensive metaphyseal and diaphysial bone loss and damage has required resection to establish a resection level at 34, leaving no calcar and a diaphysis which is not intact. The revision femoral component 32 includes an integral collar 36 which will be seated upon the natural bone of the proximal femur 30 at the resection level 34 and an elongate stem 37 will extend into the femur to compensate for the damaged diaphysis. A more extended neck portion 38 compensates for the absence of the calcar and will receive a femoral head 39 in a conventional manner.

Figure 2:
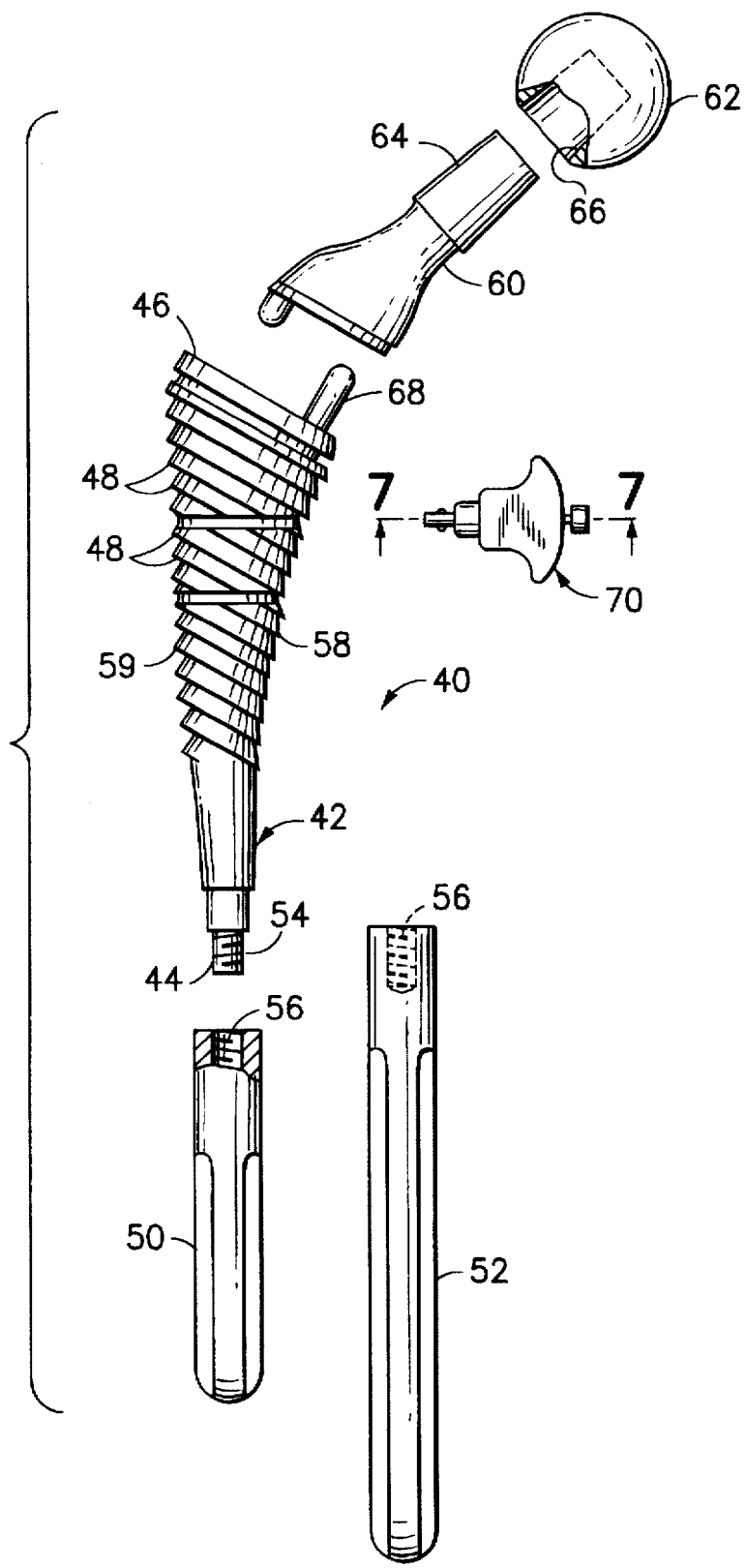
FIG. 2 is an exploded elevational view of an instrument set constructed in accordance with the present invention.

Turning now to FIG. 2, a surgical instrument set constructed in accordance with the present invention is shown at 40 and is seen to include a revision broach 42 having a distal end 44, a proximal end 46 spaced longitudinally from the distal end 44, and a multiplicity of cutting teeth 48 arranged along the greatest portion of the longitudinal length of the revision broach 42, in a now conventional manner. Any one of several distal extensions, two of which distal extensions are shown at 50 and 52, is selectively coupled with the distal end 44 of the revision broach 42, by means of a threaded stud 54 extending from the distal end 44 for reception within a complementary threaded socket 56 in the selected distal extension 50 or 52 in a conventional manner. The revision broach 42 extends laterally between a medial side 58 and a lateral side 59. A selected trial neck 60 receives a selected trial head 62, which is coupled to the trial neck 60 by the engagement of a tapered projection 64 on the trial neck 60 with a complementary tapered opening 66 in the trial head 62, in a well known manner. The trial neck 60 is selectively coupled with the proximal end 46 of the revision broach 42 by a now well-known coupling means which includes a post 68 integral with the revision broach 42 and projecting from the proximal end 46. A stop member 70 completes the illustrated set 40.

Figure 3:
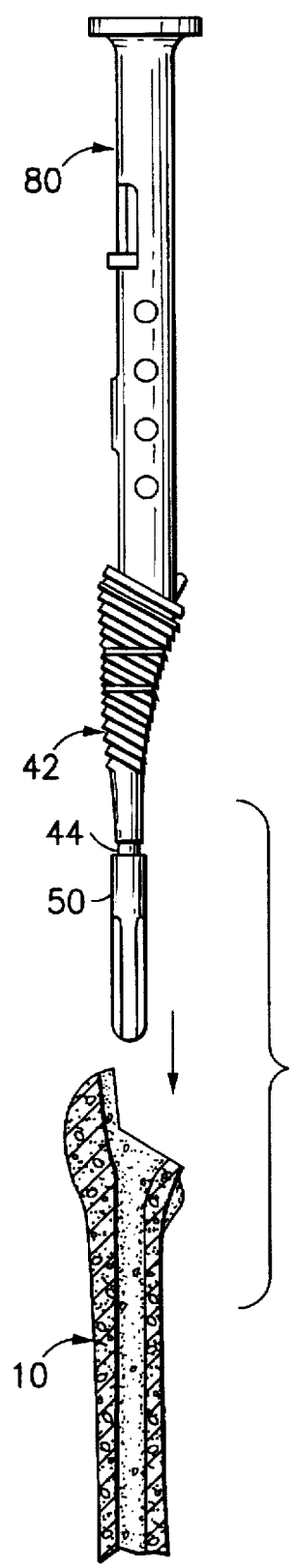
FIG. 3 is an elevational view showing a revision broach of the instrument set being inserted into a proximal femur.
Figure 4:
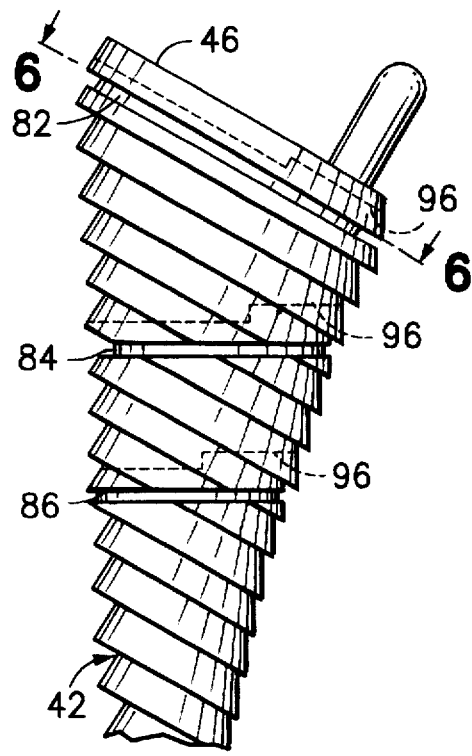
FIG. 4 is an enlarged fragmentary elevational view of a proximal portion of the revision broach.
Figure 5:
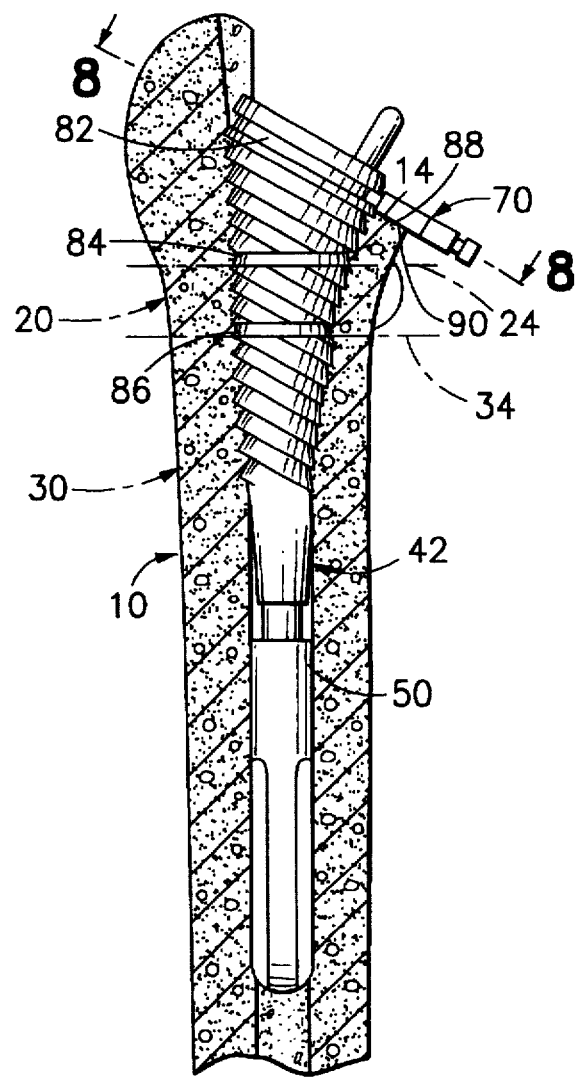
FIG. 5 is an elevational view of the revision broach in place in the proximal femur.

In order to insert revision broach 42 into a partially prepared proximal femur, such as illustrated by proximal femur 10, a selected distal extension, shown as distal extension 50, is coupled with the distal end 44 of the revision broach 42 and an operating handle 80 is coupled with the proximal end 46 of the revision broach 42, as seen in FIG. 3. Operating handle 80 has a now-conventional construction, an example of which is disclosed in U.S. Pat. No. 4,765,328, and is coupled to the revision broach 42 in a known manner for assistance in the insertion of the revision broach 42 into the proximal femur 10. As best seen in FIG. 4, revision broach 42 is provided with a series of visible gage marks shown in the form of resection grooves 82, 84 and 86 spaced apart longitudinally along the revision broach 42 and extending laterally across the revision broach 42 from the medial side 58 to the lateral side 59 to correspond with the resection levels 14, 24 and 34, respectively. That is, when the resection broach 42 is inserted into proximal femur 10, prepared with a resection level 14, the revision broach 42 is inserted until a position is reached where the resection groove 82 is juxtaposed with the resection level 14, as shown in FIG. 5. The same revision broach 42 can be used to prepare proximal femur 20 or proximal femur 30; however, in the case of proximal femur 20, the revision broach 42 is inserted until the corresponding resection groove 84 is juxtaposed with the resection level 24, as shown in phantom in FIG. 5, and in the case of proximal femur 30, the revision broach 42 is inserted until the corresponding resection groove 86 is juxtaposed with the resection level 34, also as shown in phantom in FIG. 5. In every case, the revision broach 42, with the selected distal extension 50 or 52 assembled thereto, mimics the appropriate revision femoral implant component 12, 22 or 32, and the location of the revision broach 42 in the proximal femur 10, 20 or 30 emulates the location of the appropriate revision femoral implant component 12, 22 or 32.

Once the revision broach 42 is fully inserted to the proper location indicated by the juxtaposition of one of the resection grooves 82, 84 or 86 with a corresponding resection level 14, 24 or 34, stop member 70 is attached to the revision broach 42, and operating handle 80 is detached from the proximal end 44, as seen in FIG. 5. Proper seating of the revision broach 42 at the location where the revision broach 42 emulates the location of the femoral implant component 12, 22 or 32 to be implanted, is assured and maintained by such attachment of the stop member 70, with the stop member 70 abutting the prepared bone at 88.

Figure 6:
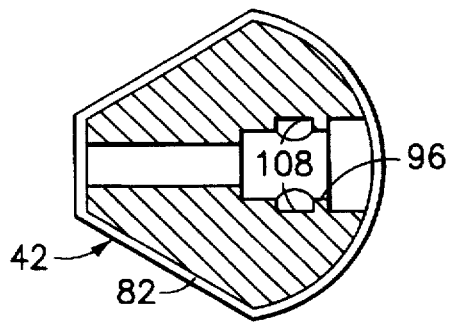
FIG. 6 is a cross-sectional view taken along line 6—6 of FIG. 4.
Figure 7:
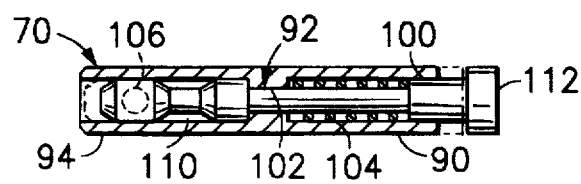
FIG. 7 is an enlarged cross-sectional view taken along line 7—7 of FIG. 2.
Figure 8:
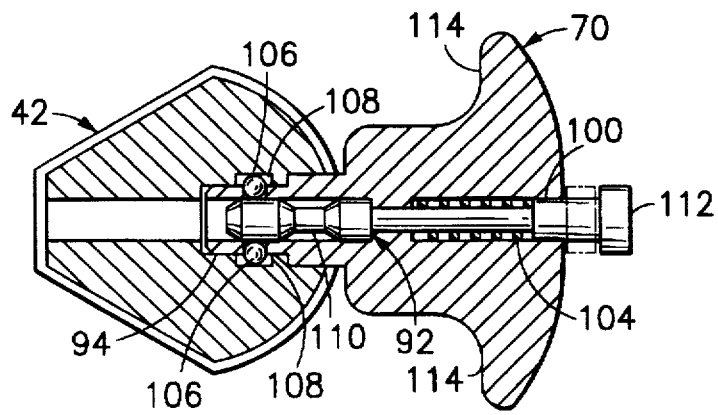
FIG. 8 is an enlarged cross-sectional view taken along line 8—8 of FIG. 5.

Referring now to FIGS. 6 through 8, stop member 70 includes a relatively broad and flat lower face 90 for confronting the prepared bone at the resection level 14 of the proximal femur 10 and complementary engagement of the stop member 70 with the proximal femur 10 at the resection level 14. Stop member 70 is attached to the revision broach 42 by attachment means shown in the form of a quick-connect mechanism 92 having attachment elements including interengagable securing members having complimentary configuration. Thus, the attachment means includes a first attachment element having a shape in the form of a projection 94 on the stop member 70 and second attachment elements each having a shape in the form of identical complementary sockets 96 spaced longitudinally along the revision broach 42 such that each socket 96 is aligned with a corresponding resection groove 82, 84 or 86. The sockets 96 are placed along the medial side 58 of the revision broach 42 and are oriented such that each socket 96 follows the lateral direction of the corresponding resection groove 82, 84 or 86, so that upon attachment of the stop member 70, the lower face 90 is aligned for proper abutment with the prepared bone at the corresponding resection level 14, 24 or 34.

The quick-connect mechanism 92 further includes a manually operated plunger 100 mounted in the stop member 70 for sliding movement within a bore 102 and biased toward a rest position, as shown in full lines in FIGS. 7 and 8, by a compression spring 104. In the rest position, a pair of locking projections, in the form diametrically opposed balls 106 carried in the stop member 70, are urged radially outwardly to extend outwardly from the projection 94 and enter diametrically opposed complementary depressions 108 in the socket 96 to secure the projection 94 within the socket 96. The complementary depressions 108 are located so that in addition to securing the projection 94 against withdrawal from the selected socket 96, the complementary depressions 108 secure the stop member 70 against rotation within the socket 96 to maintain face 90 of the stop member 70 in complementary confronting relationship with the prepared bone at resection level 14. Upon manual actuation of the plunger 100 to move the plunger 100, against the bias of the compression spring 104, to a second position, as seen in phantom in FIGS. 7 and 8, an annular recess 110 in the plunger 100 is registered with the balls 106, enabling the balls 106 to move radially inwardly and out of the depressions 108, thereby freeing the projection 94 for movement out of the socket 96. Manual actuation of the plunger 100 is facilitated by the provision of a thumb pad 112 at the protruding end of the plunger 100 and diametrically opposed finger grips 114 on the stop member 70, enabling the surgeon to grasp the stop member 70 and actuate the plunger 100 in a manner with which physicians are well acquainted.

Figure 9:
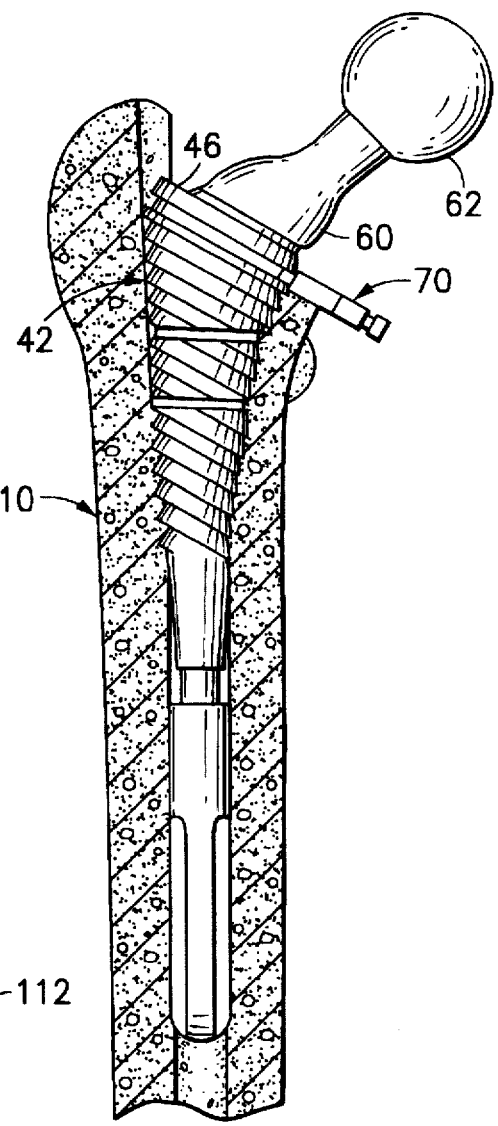
FIG. 9 is an elevational view showing a trial neck and trial head in place at the proximal end of the revision broach.

Once the revision broach 42 is fully seated within the proximal femur 10, with the stop member 70 attached to assure that proper seating is maintained, the selected trial neck 60 and the selected trial head 62 are coupled with the proximal end 46 of the revision broach 42, as seen in FIG. 9, for subsequent trial reduction. Upon completion of the trial reduction, the trial neck 60 and the trail head 62 are released and removed from the proximal end 42 and operating handle 80 once again is coupled with the revision broach 42 for removal of the revision broach 42 and subsequent insertion of the selected revision femoral implant component and coupling of the femoral head to the femoral implant component, as set forth above.

It will be seen that the present invention attains the several objects and advantages summarized above; namely: Provides a surgical instrument set incorporating a single revision broach which enables mimicking any one of a plurality of revision femoral implant components constructed to compensate for different deficiencies encountered in a proximal femur, for the conduct of trial reduction with the revision broach in place in the proximal femur; simplifies the revision procedure, enabling reduced operating time, with concomitant benefits to the patient; attains increased accuracy and precision in the location of an appropriate revision femoral implant component, without the necessity for multiple revision broaches to accommodate different conditions encountered at the implant site; provides a visual indication of the appropriate location of the single revision broach in the proximal femur, and maintaining seating of the revision broach at that location for the subsequent conduct of trial reduction; reduces the expense and complexity of a set of surgical instruments utilized for revision surgery; facilitates the revision surgery procedure.

It will be apparent that while the instrument set 40 has been described in connection with revision surgery, the instruments of instrument set 40 can be utilized in connection with the implant of a primary femoral implant component where conditions encountered at the proximal femur warrant the use of such instruments.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. An improvement in a surgical instrument set for the preparation of a proximal femur during surgery to receive a selected one femoral implant component of a plurality of available femoral implant components provided to accommodate a corresponding one of a plurality of resection levels determined by the condition of the proximal femur, the improvement comprising:

a broach having a distal end for the reception of a selected distal extension to mimic the selected one femoral implant component, and a proximal end spaced longitudinally from the distal end for alternately receiving an operating handle for insertion of the broach into the proximal femur, and a trial neck and a trial head for conducting a trial reduction;

a stop member; and selective attachment means for selectively attaching the stop member to the broach at any one selected location of a plurality of locations spaced longitudinally along the broach, the plurality of locations corresponding to the plurality of resection levels such that the stop member is juxtaposed with the proximal femur when the broach is at a location which emulates the location of the selected femoral implant component and maintains the broach seated at that location for reception of the trial neck and the trial head and subsequent trial reduction.

2. The invention of claim 1 wherein the selective attachment means includes;

a first attachment element on the stop member, the first attachment element having a configuration; and a plurality of second attachment elements spaced longitudinally along the broach;

each one of the plurality of second attachment elements having a configuration complementary to the configuration of the first attachment element and being located such that the stop member, when attached to the broach at said any one selected location, is placed at a corresponding one of the plurality of resection levels for juxtaposition with the proximal femur when the broach is at the location which emulates the location of the selected femoral implant component.

3. The invention of claim 2 wherein the broach includes a lateral side and a medial side, and the plurality of second attachment elements are located along the medial side.

4. The invention of claim 2 wherein the first attachment element includes a projection on the stop member and the second attachment elements each include a socket in the broach, the projection having a shape and each socket having a shape complementary to the shape of the projection for receiving the projection within the socket upon attachment of the stop member to the broach.

5. The invention of claim 4 wherein each socket is oriented to orient the stop member for abutment with the proximal femur at the corresponding resection level.

6. The invention of claim 5 wherein the stop member includes an essentially flat face for confronting and engaging the proximal femur at the corresponding resection level.

7. The invention of claim 5 wherein the selective attachment means comprises a quick-connect mechanism, the first and second attachment elements including complementary interengagable securing members, and a manually operated actuator for selective operation to engage and disengage the complementary interengagable securing members.

8. The invention of claim 1 including visible gage marks at each of the plurality of locations spaced longitudinally along the broach.

9. The invention of claim 8 wherein the broach includes a lateral side and a medial side, and each visible gage mark includes a groove extending laterally across the broach between the medial side and the lateral side.

10. An improvement in a method for the preparation of a proximal femur during surgery to receive a selected one femoral implant component of a plurality of available femoral implant components provided to accommodate a corresponding one of a plurality of resection levels determined by the condition of the proximal femur, the improvement comprising the steps of:

coupling a selected distal extension and an operating handle to a broach having a distal end for the reception of the selected distal extension to mimic the selected one femoral implant component, a proximal end spaced longitudinally from the distal end for alternately receiving the operating handle and a trial neck and a trial head, and selective attachment means providing a plurality of attachment locations spaced longitudinally along the broach, the plurality of locations corresponding to the plurality of resection levels;

inserting the broach into the proximal femur and placing the broach at a location where the corresponding one of the plurality of attachment locations is placed at the selected one of the plurality of resection levels so as to emulate the location of the selected femoral implant component in the proximal femur;

attaching a stop member to the broach at the one of the plurality of attachment locations corresponding to the one of the plurality of resection levels for maintaining the broach seated at the location which emulates the location of the selected femoral implant component;

detaching the operating handle from the proximal end of the broach; and attaching the trial neck and the trial head to the proximal end of the broach for subsequent trial reduction.

11. The invention of claim 10 including:

subsequently detaching the trial neck and the trial head from the proximal end of the broach;

subsequently re-attaching the operating handle to the proximal end of the broach;

then removing the broach from the proximal femur; and then inserting the femoral implant component.

12. The invention of claim 11 including coupling a femoral head to the femoral implant component.

* * * * *